US008784788B2

(12) United States Patent
Pliszka

(10) Patent No.: US 8,784,788 B2
(45) Date of Patent: Jul. 22, 2014

(54) GEL CARRIER FOR RELEASING ACTIVE INGREDIENTS

(75) Inventor: Matthew E. Pliszka, Germantown, WI (US)

(73) Assignee: Environmentally Sensitive Solutions, Inc., Mequon, WI (US)

( * ) Notice: Subject to any disclaimer, the term of this patent is extended or adjusted under 35 U.S.C. 154(b) by 0 days.

(21) Appl. No.: 13/428,998

(22) Filed: Mar. 23, 2012

(65) Prior Publication Data
US 2012/0251477 A1 Oct. 4, 2012

Related U.S. Application Data

(60) Provisional application No. 61/468,984, filed on Mar. 29, 2011.

(51) Int. Cl.
C02F 3/34 (2006.01)

(52) U.S. Cl.
USPC ........................................................ 424/76.5

(58) Field of Classification Search
CPC .................................................... C11D 3/2086
USPC ........................................................ 424/76.5
See application file for complete search history.

(56) References Cited

U.S. PATENT DOCUMENTS

| | | |
|---|---|---|
| 4,283,300 A | 8/1981 | Kurtz |
| 4,302,350 A | 11/1981 | Callicott |
| 4,428,872 A | 1/1984 | Callicott |
| 4,452,713 A | 6/1984 | Small |
| 4,655,794 A | 4/1987 | Richardson et al. |
| 4,666,671 A | 5/1987 | Purzycki et al. |
| 5,095,058 A | 3/1992 | Smith et al. |
| 5,188,755 A | 2/1993 | Chang |
| 5,284,587 A * | 2/1994 | Wong et al. .................... 210/606 |
| 5,543,309 A | 8/1996 | Pischel |
| 5,578,089 A | 11/1996 | Elsamaloty |
| 5,783,657 A | 7/1998 | Pavlin |
| 5,813,058 A | 9/1998 | Quigley et al. |
| 5,958,758 A | 9/1999 | Miller et al. |
| 5,977,050 A | 11/1999 | Faris |
| 6,242,509 B1 * | 6/2001 | Berger et al. .................. 523/122 |
| 6,410,305 B1 | 6/2002 | Miller et al. |
| 6,503,077 B2 | 1/2003 | Orth et al. |
| 6,864,349 B2 | 3/2005 | Pavlin et al. |
| 6,884,351 B1 | 4/2005 | Lytal |
| 7,544,298 B1 | 6/2009 | Chanley |
| 7,709,433 B2 | 5/2010 | Veltman et al. |
| 7,854,843 B2 | 12/2010 | Pehrson et al. |
| 7,858,336 B1 | 12/2010 | Garner et al. |

OTHER PUBLICATIONS

Lin et al (Isolation and characterization of a new heterotrophic nitrifying *Bacillus* sp. strain. Biomed Environ Sci. Dec. 2007;20(6):abstract).*

International Search Report issued for PCT/US12/30587; mailed Jun. 28, 2012.

* cited by examiner

*Primary Examiner* — Jake Vu

(74) *Attorney, Agent, or Firm* — Brian G. Gilpin; Godfrey & Kahn, S.C.

(57) ABSTRACT

A gel carrier for releasing active ingredients is formed from a co-polymer blend and an active ingredient blend. The co-polymer blend and active ingredient blend are combined and allowed to cool to a desired temperature. When the gel carrier floats in, is immersed, or is exposed to water-based materials, active ingredients are leached out of the gel carrier.

1 Claim, 6 Drawing Sheets

GEL CARRIER FOR RELEASING ACTIVE INGREDIENTS

PRIORITY CLAIM AND CROSS-REFERENCE TO RELATED APPLICATION

This application is based on and claims priority to U.S. provisional patent application Ser. No. 61/468,984 filed on Mar. 29, 2011, which is incorporated herein by reference in its entirety for all purposes.

FIELD OF THE INVENTION

The present invention relates generally to the field of carriers for dispensing microorganisms or other active ingredients over a period of time. More particularly, the present invention relates to a semi-rigid co-polymer gel formulation and dispensing method for releasing microorganisms or other agents over time into water-based liquids.

BACKGROUND

It is well known that the activities of microorganisms and compounds produced by microorganisms can sometimes be used as safer and more environmentally friendly alternatives to synthetic or chemical products in a variety of applications, including, but not limited to, applications to remediate grease and oil, remove animal waste, clarify pondwater, or prevent blockages in waste lines. In applications where microorganism based products can be used instead of, or in addition, to synthetic or chemical agents, one frequently encountered problem is how to release the microorganisms or other desirable ingredients over time. Other common problems encountered when releasing microorganism based products or other active ingredients over time include preserving the viability of microorganisms or efficacy of the active ingredients and providing a stable carrier for the microorganisms or active ingredients.

Accomplishing the release over time of desired ingredients has been accomplished previously by relying on a specific physical form to dictate the speed of release. Products accomplishing the release over time of desired ingredients usually take the form of powders (see e.g., EP 0014979), formulated into solid blocks or pucks (e.g., U.S. Pat. Nos. 4,283,300, 4,302,350, 4,428,872, 4,452,713, 4,666,671, 5,188,755), formulated into gels (e.g., U.S. Pat. No. 7,709,433) or put into liquids (e.g., U.S. Pat. Nos. 4,655,794, 5,977,050). Known methods for disseminating microorganisms include: powders or liquids containing microorganisms and/or enzymes which may be dispensed for example by hand or water-soluble pouches. See, e.g., U.S. Pat. Nos. 6,884,351; 5,543,309; 6,410,305; 5,958,758; 7,858,336. Additionally, solid blocks or screens have been used (see, e.g. U.S. Pat. No. 5,813,058), as well as mechanical apparatus and devices used to try to control the release of microorganisms (see, e.g., U.S. Pat. Nos. 7,854,843; 7,544,298).

These previously known methods, however, fall short in releasing active ingredients consistently over a period of time. The key performance traits needed when delivering microorganisms are continual release over time, as well as the ability to have the microorganisms release in a desired location (usually at the surface of the treatment area). While previously known methods may work effectively for dispensing certain chemical ingredients exclusively, they often times do not provide a hospitable environment for the viability of microorganisms (chemical effects can significantly reduce or totally eliminate microorganism colony forming units per gram) or enzymes (chemical effects can denature enzymes easily). Another reason they have not been effective is that the microorganisms are released too quickly or all at once, making their performance spike and fall off before the desired task has been completed. Simply adding microorganisms and enzymes to known delivery systems is also an insufficient solution because of chemical incompatibilities, improper product pH, inability to preserve organism viability, and the harsh conditions of manufacturing processes.

As such, a need exists for a carrier for releasing active ingredients in which the format of the delivery system and method for manufacturing preserve the viability of microorganisms and activity of enzymes and other active ingredients. The disclosed gel carrier for releasing active ingredients serves as a carrier for microorganisms, enzymes, and other active ingredients, and when the gel is floating-in, immersed, or subjected to periodic exposure to water-based materials, active ingredients are released from the gel. The disclosed gel carrier also maintains the viability of microorganisms and other sensitive compounds because such compounds are not subjected to harsh manufacturing processes or conditions.

It will be understood by those skilled in the art that one or more aspects of this invention can meet certain objectives, while one or more other aspects can lead to certain other objectives. Other objects, features, benefits and advantages of the present invention will be apparent in this summary and descriptions of the disclosed embodiment, and will be readily apparent to those skilled in the art. Such objects, features, benefits and advantages will be apparent from the above as taken in conjunction with the accompanying figures and all reasonable inferences to be drawn there from.

DETAILED DESCRIPTION

Figure 1:
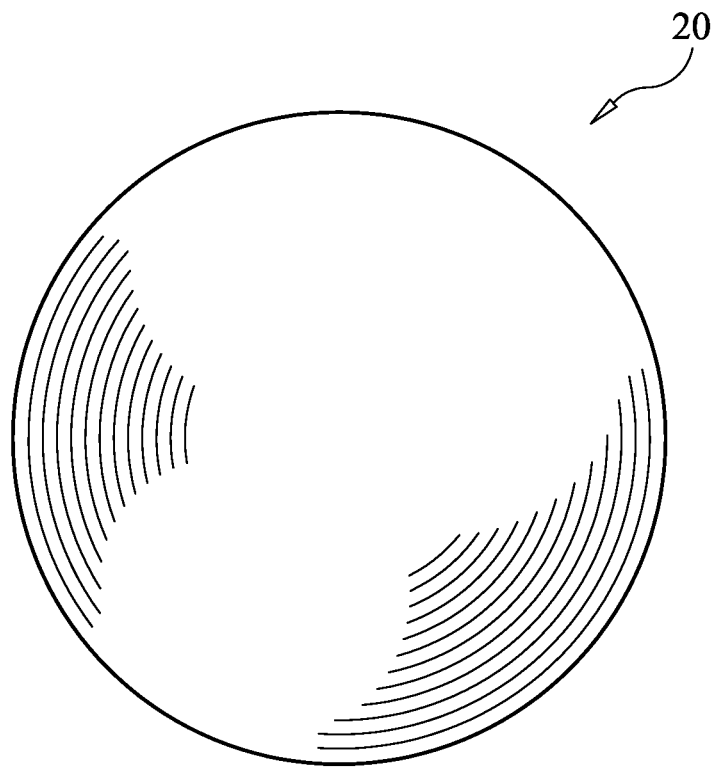
FIG. 1 is a perspective view of an embodiment of a gel carrier for releasing active ingredients for use in a urinal, in the shape of a ball.

A gel carrier releases active ingredients when floating-in, immersed, or periodically subjected to water-based liquids. The gel carrier could be used to disseminate active ingredients in a variety of applications, including but not limited to: urinal and toilet care, lift station maintenance, grease trap maintenance, wastewater treatment, aquaculture, pond care, waste holding tank treatment, portable toilets, oil spill clean-up, and other applications where it will be useful to introduce and disseminate active ingredients over a period of time. Active ingredients may include microorganisms, spores, surfactants, chelants, enzymes, sulfur-binders, preservatives, nutrients, or any other water soluble, semi-soluble, or water-miscible compounds that can be mixed into a gel.

A gel carrier in accordance with the present invention includes: (1) a co-polymer blend, which forms a gel matrix; and (2) an active ingredient blend, which contains any desired active ingredients. The gel matrix is a stable compound and tolerates a wide variety of active ingredients. The gel matrix is not water soluble, so when the gel carrier is subjected to water-based materials, active ingredients are leached out of the gel carrier. Because the gel matrix in the gel carrier is not water soluble, it can resist water flow and immersion better than water soluble alternatives such as hydrolyzed polyacrylamides, polymers, and copolymers, stearates and other ingredients that dissolve in water used in other products. In addition, the releasing of ingredients from the gel matrix occurs in stagnant water, which is something that other water soluble alternatives cannot readily achieve. This gives the gel carrier superior continual release properties when compared to water soluble alternatives.

Conventional dispensing methods use water soluble materials as carriers for active ingredients that dissolve in order to release the active ingredients. This is less than ideal because rates of active ingredient release will directly depend on application conditions, such as whether the water is stagnant or flowing, the water flow rate, the solids content of the water, and the temperature of the water. These conditions result in active ingredient release rates that fluctuate wildly as those conditions change, resulting in inconsistent release rates over time. The gel carrier releases active ingredients in a much more controlled manner with release rates that are far less dependent on the conditions of the application conditions because it does not rely on the carrier itself to dissolve in order to release the active ingredients.

In conventional applications of co-polymer gels, the leaching of ingredients is normally thought of as an undesirable property, but it has been discovered that this property is advantageous when used as described herein because it allows for the controlled release of active ingredients in environments in which it has previously been difficult to achieve this result. For example, when co-polymer gels are used in applications such as candles where burning the candle is used as a controlled release method for emitting fragrance into the air, leaching of substances prior to or without burning is an undesirable property. See, e.g., U.S. Pat. Nos. 5,578,089; 5,783,657, 6,864,349. Also, unlike candle applications, the gel carrier for releasing active ingredients is used in completely different environments, namely immersed in, floated on, or subjected to periodic exposure to flows of water-based materials (for example, urine, waste water, lakes or ponds, or sewage).

The use of a gel carrier is also advantageous because it provides an environment that preserves the efficacy of the active ingredients. For example, a gel carrier for microbial active ingredients will provide a pH that is compatible with microorganism spore survival and will maintain near 100% spore viability through the manufacturing process. The gel carrier is prepared by combining the co-polymer blend and the active ingredient blend. This process is discussed in more detail below, but it occurs at temperatures which preserve the desired properties or viability of the active ingredients.

The gel carrier for releasing active ingredients is used by placing it in a location where it floats-in, is immersed in, or is periodically subjected to water-based liquids. When the gel carrier contacts the water-based liquids, active ingredients leach out of the gel carrier and into the water-based liquid, where the active ingredients can accomplish the desired affect. Several embodiments of gel carriers for releasing active ingredients are discussed below. After all or nearly all of the active ingredients have been dispensed from the gel carrier, the gel carrier can be formulated by adjusting the relative amounts of the various ingredients in the co-polymer blend and the active ingredient blend to allow the gel carrier to crack and break apart when most of the active ingredients have leached out of the gel carrier. This cracking or breaking apart serves the dual purposes of increasing the exposed surface area of the gel carrier to allow the remaining active ingredients to be more consistently released from the gel carrier, but also to provide a visual cue to the user that the gel carrier should be replaced. The performance life of the gel carrier will vary depending on the formulation of ingredients used, and the application, but the gel carrier commonly will dispense active ingredients for a period of 1-6 weeks.

To manufacture a gel carrier for releasing active ingredients, co-polymer blend and active ingredient blends are prepared and mixed together while the co-polymer blend is cooling.

For the co-polymer blend, various types of co-polymers can be used, independently or in combination with other ingredients. Co-polymers used for a gel carrier for releasing active ingredients should preferably: 1) be mostly or completely insoluble in water; 2) capable of forming a semi-rigid gel that can hold a molded shape; 3) capable of forming internal three dimensional networks due to cross-linking once the gel has formed; 4) capable of tolerating some water content; and 5) should exhibit low or no syneresis. Syneresis refers to the property of some co-polymer gels in which liquid from the gel matrix separates or is released so that liquid droplets or puddles form on the exterior of the gel surface. Syneresis is undesirable because it can lead to a premature release of active ingredients before the gel carrier is used in the desired application. Commonly, co-polymer blends will include a polyamide or other type of gel and a non-polar solvent, as well as possibly surfactants and water.

Procedures to make co-polymer gels are well known in the art (see, e.g., U.S. Pat. Nos. 5,095,058; 5,578,089; 5,783,657; 6,503,077 and others). Depending on the particular co-polymer used, the specific ingredients for preparing a co-polymer blend will vary. To prepare the co-polymer blend, usually the co-polymer is melted in a hot process or prepared generally in accordance to manufacturer instructions. The co-polymer blend is then combined with the active ingredient blend which contains the active ingredients desired for a particular application and any solvents.

An active ingredient blend is usually comprised of the desired active ingredients and water or other liquid. Active ingredients can include, but are not limited to microorganisms, spores, surfactants, chelants, enzymes, sulfur-binders, preservatives, nutrients, or any other water soluble or semi-soluble compounds that can be mixed into a gel. The active ingredient blend is combined with the co-polymer blend and mixed gently.

Figure 2:
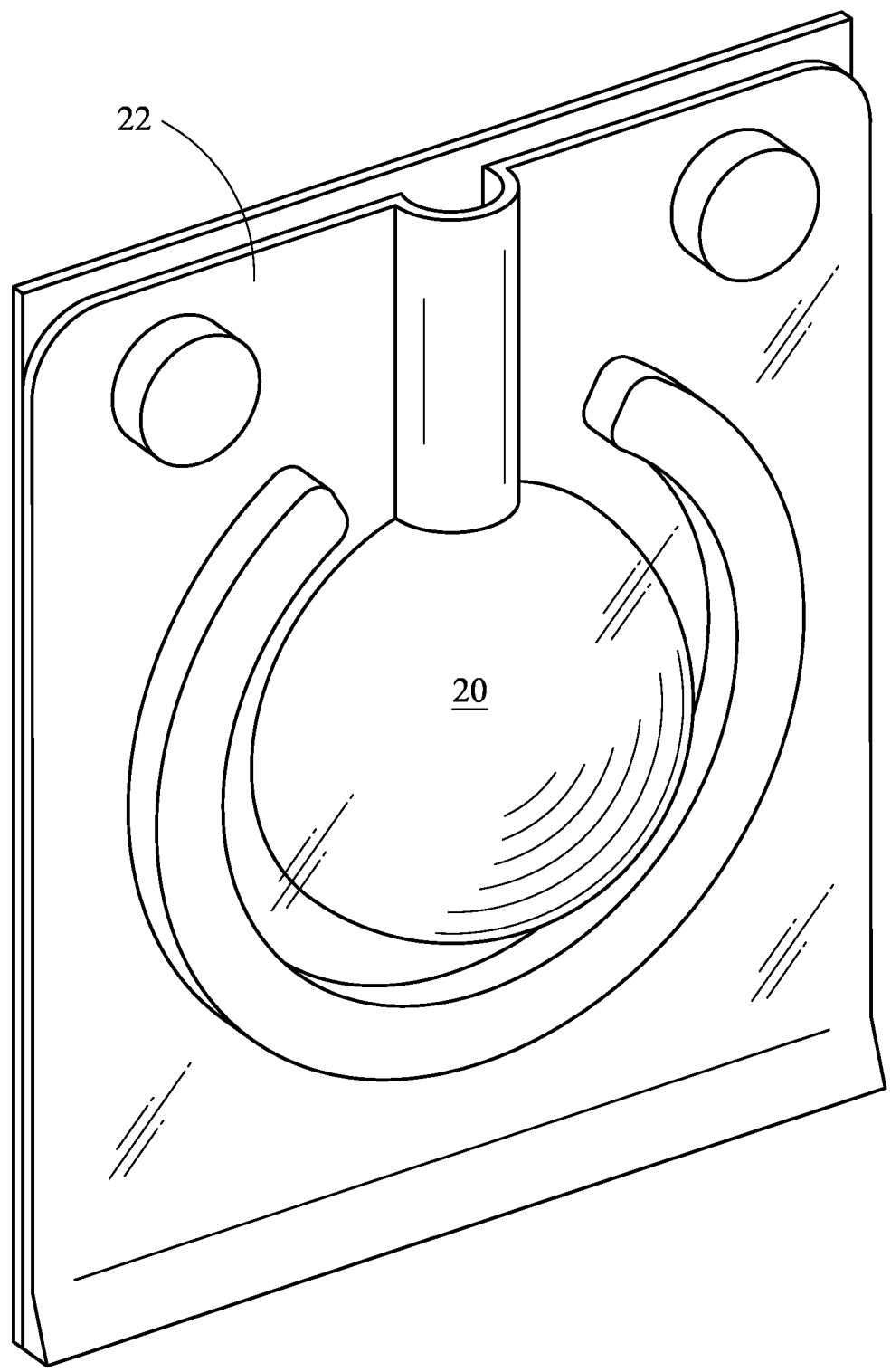
FIG. 2 is a perspective view of the gel carrier ball of FIG. 1, shown in clam-shell style packaging.
Figure 3:
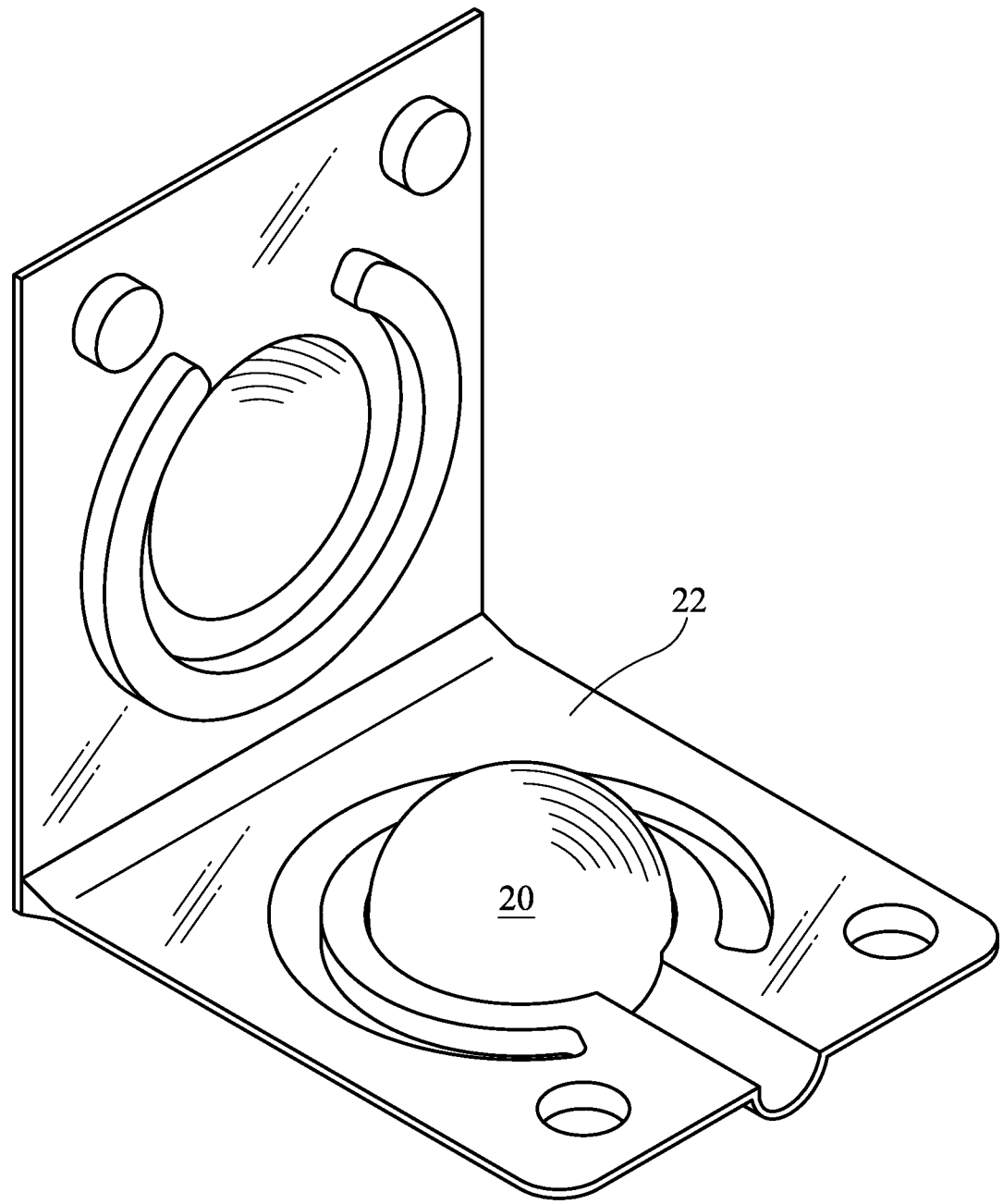
FIG. 3 is a perspective view of the gel carrier ball and clam-shell style packaging photograph of FIG. 2, showing the clam-shell style packaging in an open position.

The combined co-polymer blend and active ingredient blend are allowed to cool to room temperature or allowed to polymerize in a mold or container, which causes the gel carrier to become a semi-rigid solid gel that will retain the desired shape of the mold or container. In one particularly efficient embodiment, the combined co-polymer blend and active ingredient blend can be inserted into a clam shell style plastic container 22 that serves both as the mold for cooling, and the retail packaging. An example of this type of application is shown in FIGS. 1-3.

The co-polymer blend and the active ingredient blend are combined when the co-polymer blend is at a temperature at which the co-polymer blend is fluid. Typically, the temperature of the prepared co-polymer blend is warmer than the temperature of the prepared active ingredient blend, thus when they are combined, the temperature of the combined materials drops. The combined co-polymer blend and active ingredient blend is allowed to cool further until it reaches a semi-rigid state or until a desired temperature. Commonly the prepared co-polymer blend can be combined with the prepared active ingredient blend immediately after preparation. For several common co-polymers that would be suitable for use in a gel carrier, the temperature of the prepare co-polymer blend would be about 180 degrees Fahrenheit or greater and can be combined with the active ingredient blend at this temperature without significant degradation or loss of performance of the active ingredients.

While the gel carrier is cooling, it can be molded into any desired shape using a pre-formed mold. Such molds may be designed in an infinite number of shapes, but one aesthetically pleasing and functionally effective form for gel carriers for urinal applications is to form the gel carrier in a ball 20 or generally round shape. See, e.g., FIGS. 1-3. Once cooled to room temperature, the gel carrier becomes a semi-rigid solid gel that will retain the desired molded shape over time and the performance life of the device, and that will float in or otherwise be subjected to liquids that are mostly water.

The semi-rigid gel carrier solidifies in such a way that the other ingredients remain mixed homogeneously through the gel carrier over time and the performance life of the product. When not in use in a particular application, there is no significant separation, degradation, or stratification of ingredients in the gel carrier over time. In addition, the semi-rigid co-polymer gel does not lose its desired shape when stored over time.

The following are examples of possible co-polymer blend formulations that could be used in a gel carrier in accordance with the present invention. Relative weight percentages are based on the total weight of the completed gel carrier (including both the co-polymer blend and the active ingredient blend). Representative suppliers of the components are identified but other components with similar characteristics and other suppliers could be used without departing from the invention. These examples are not exclusive, there are many additional formulations that could be used as suitable co-polymer blends without departing from the invention:

Co-polymer Blend Example 1:
Polyamide gel SYLVACLEAR® SERIES (Arizona Chemical Company) at 10-40% by weight as the co-polymer and GLYCOL ETHER TPM (Dow Chemical) at 10-30% by weight and PROPYLENE GLYCOL (Dow Chemical) at 10-30% by weight as a polar solvent blend, heated to a minimum of 180° F. and mixed.

Co-polymer Blend Example 2:
Blend of block co-polymers KRATON® A SERIES (Kraton Polymers, LLC) at 1-10% by weight as the co-polymer and GLYCOL ETHER TPM (Dow Chemical) at 10-50% by weight as a polar solvent, heated to a minimum of 220° F. and mixed.

Co-polymer Blend Example 3:
Blend of block co-polymer VERSAGEL® C SERIES (Penereco) at 1-20% by weight as the co-polymer and GLYCOL ETHER TPM (Dow Chemical) at 2-50% by weight as a solvent, heated to 240° F. and mixed.

Figure 4:
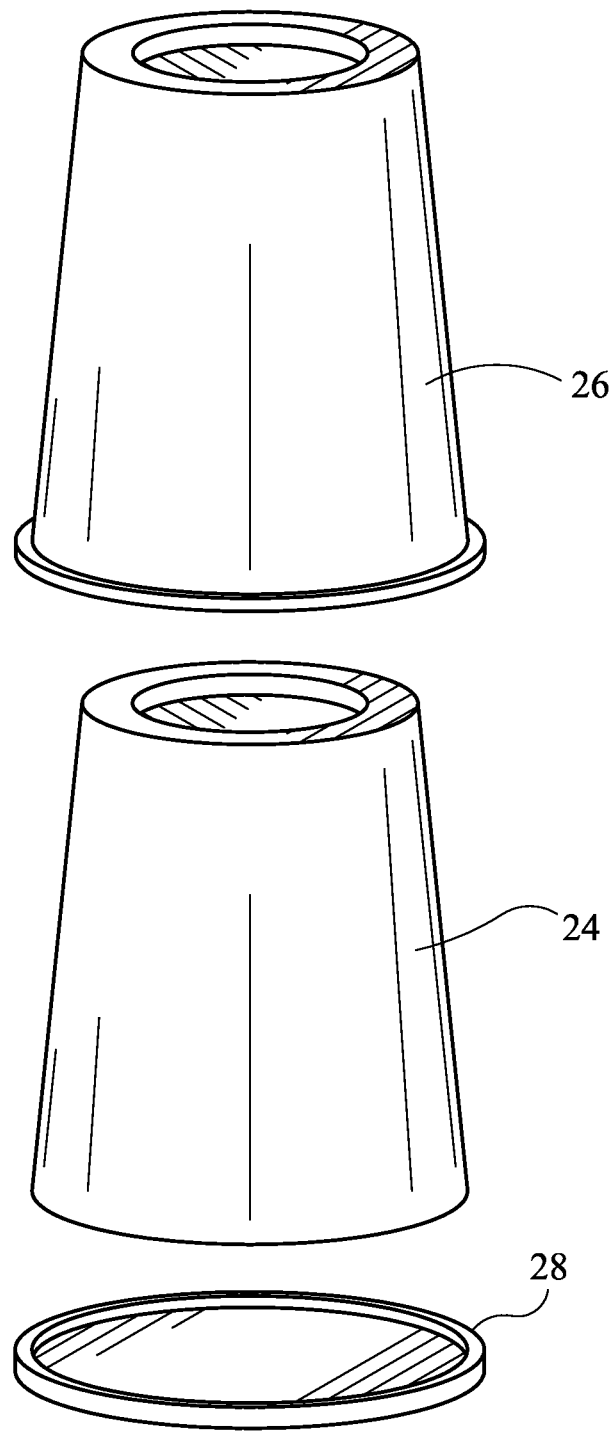
FIG. 4 is an exploded perspective view of an embodiment of a gel carrier for releasing active ingredients for use in a lift station, shown positioned outside the mold in which it was formed.
Figure 5:
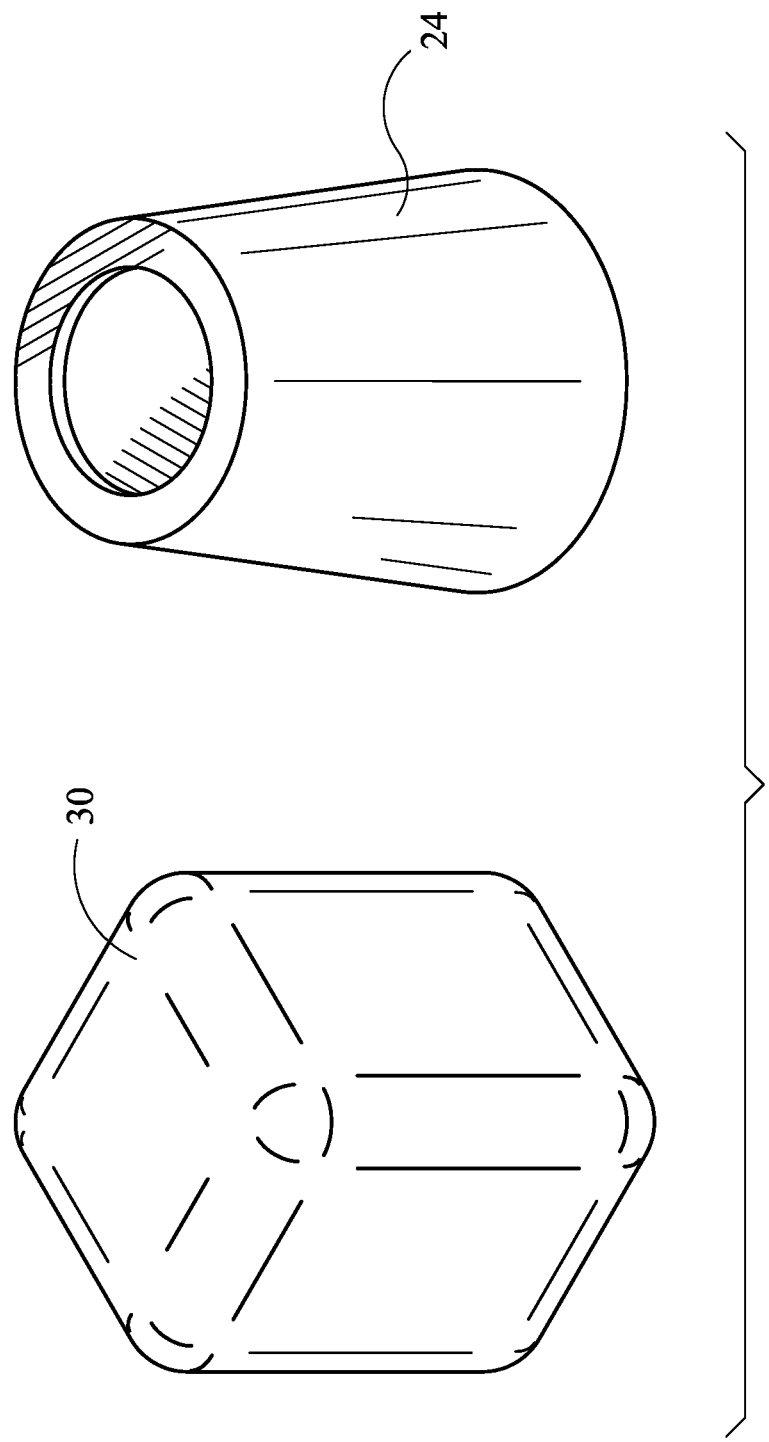
FIG. 5 is a perspective view of two additional embodiments of gel carriers for releasing active ingredients for use in lift stations.

The following are examples of possible active ingredient blend formulations that could be used in a gel carrier in accordance with the present invention. Relative weight percentages are based on the total weight of the completed gel carrier (including both the co-polymer blend and the active ingredient blend). Representative suppliers of the components are identified but other components with similar characteristics and other suppliers could be used without departing from the invention. These examples are not exclusive, there are many additional formulations that could be used as suitable active ingredient blends without departing from the invention:

Active Ingredient Blend Example 1 (for Treating Grease Traps and Lift Stations):
Mix PURIFIED WATER at 10.0-30.0% by weight, BACILLUS BACTERIA (Microbial Discovery Group) at 1.0-20.0% by weight, SULFREE WS SERIES SULFUR BINDER (Guard Products) 0.1-4.0% by weight, VIDET Q-3 SURFACTANT (Vitech International) at 0.1-5.0%. Once mixed, add to co-polymer blend, mix again and fill desired mold or container. This embodiment could be hot molded into a block of virtually any shape, placed in a holder like a mesh bag, and placed into the lift station or grease trap. For example, FIGS. 4 and 5 show embodiments of gel carriers for use in lift stations where the gel carrier is formed into a cylindrical block shape 24 or a cube shape 30. FIG. 4 shows the cylindrical block shape 24 and the mold 26 and lid 28 that create it. The desired ingredients would be released from the co-polymer matrix in a controlled way over time in order to reduce the build up of grease and oils, control odor as well as help to prevent pipe corrosion.

Active Ingredient Blend Example 2 (for Treating Urinals):
Mix PURIFIED WATER at 10.0-30.0% by weight, BACILLUS BACTERIA (Microbial Discovery Group) at 1.0-20.0% by weight, VIDET Q-3 SURFACTANT (Vitech International) at 0.1-5.0%, FRAGRANCE (Hogan Fragrances), 0.1-2.0%, DYE (Keystone) in trace amounts. Once mixed, add to co-polymer blend, mix again and fill desired mold or container. This embodiment could be used in both flush and waterless urinals to deliver a treatment for preventing pipe blockages, and could act as a cleaning agent, as well as prevent unpleasant odors. The embodiment could be hot molded into a ball 20 (see, e.g., FIGS. 1-3), block, puck or customized to almost any shape and placed in the urinal so that with each flush or urination, the desired ingredients would dispense out of the co-polymer matrix into the urinal trapway and piping, attacking the hair and organic buildup that can often lead to slowing the flow or plugging, particularly in waterless urinals.

Figure 6:
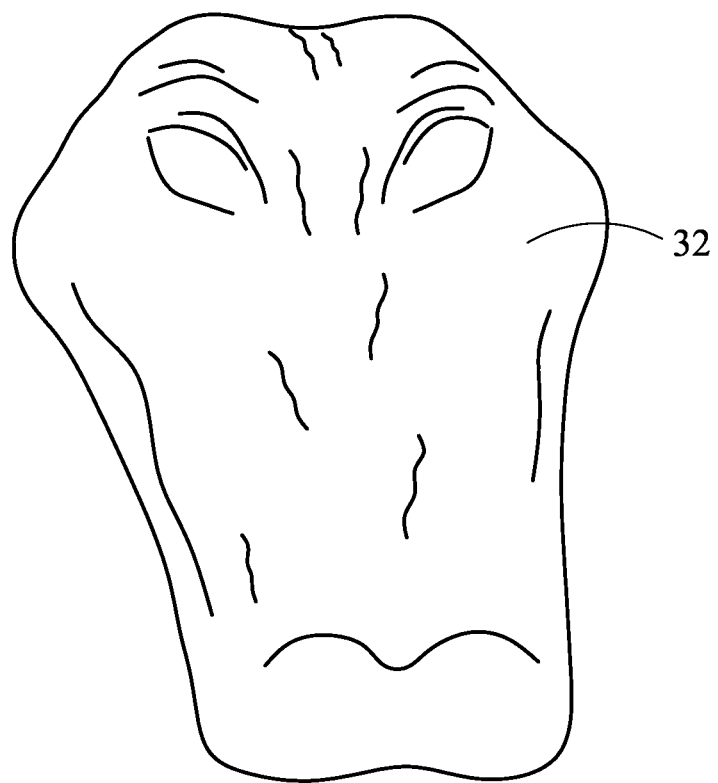
FIG. 6 is a perspective view of an embodiment of a gel carrier for releasing active ingredients in the shape of an alligator head for use in a pond.

Active Ingredient Blend Example 3 (for Treating Ponds):
Mix PURIFIED WATER at 10.0-30.0% by weight, BACILLUS BACTERIA (Microbial Discovery Group) at 1.0-20.0% by weight, DYE (Keystone) in trace amounts. Once mixed, add to co-polymer blend, mix again and fill desired mold or container. A variation of this embodiment could be molded into almost any desired shape, including a block, a boat, or alligator head. FIG. 6 shows an embodiment of a gel carrier for pond applications formed in the shape of an alligator head. When made to float, this embodiment would aid in the process of natural pond clarification—that is helping to clarify murky pond water that can deny a pond sunlight or oxygen, thus rendering it effectively dead. This embodiment has the primary benefit of dispensing the ingredients at the water's surface over a period of time where they are most effective.

Active Ingredient Blend Example 4 (for Wastewater Treatment):
  Mix PURIFIED WATER at 10.0-30.0% by weight, NUTRIENT BLEND (Microbial Discovery Group) at 1.0-30.0% by weight, VIDET Q-3 SURFACTANT (Vitech International) at 0.1-5.0%. Once mixed, add to co-polymer blend mix again and fill desired mold or container. This embodiment could be molded into almost any desired shape, including a boom or block shape, inserted into an appropriate holder like a mesh bag, and used in conjunction with powdered or liquid micro-organism blends as part of wastewater treatment systems. The nutrients will release in a controlled manner promoting consistent and stable micro-organism populations that can maximize waste degradation from wastewater in an efficient manner.

Active Ingredient Blend Example 5 (for Treating Toilets, Septic Systems, and/or Recreational Vehicle Waste Tanks):
  Mix PURIFIED WATER at 10.0-30.0% by weight, BACILLUS BACTERIA (Microbial Discovery Group) at 1.0-20.0% by weight, GLUCOHEPTONATE CHELANT (Milport Chemical) at 1.0-5.0%, VIDET Q-3 SURFACTANT (Vitech International) at 0.1-5.0%, FRAGRANCE (Hogan Fragrances), 0.1-2.0%, DYE (Keystone) in trace amounts. Once mixed, add to co-polymer blend, mix again and fill desired mold or container. Rather than kill microorganisms in the toilet bowl like most competitive products that contain chlorine or other biocide, this embodiment could be hot molded into any shape, placed in a holder like a mesh bag, plastic housing or other appropriate mechanical means, and placed in the water tank of a residential toilet. The desired ingredients would be released from the gel carrier with every flush, thus attacking and removing build up in the toilet bowl as well as the build up in the flush piping and rim channels without damaging components of the flush mechanisms. This controlled release would have the added benefit of extending the cleaning benefits to the sewer piping and/or septic systems, saving the user time and money from single dosing of specific products for those tasks.

Active Ingredient Blend Example 6 (for Aquaculture Applications):
  Mix PURIFIED WATER at 10.0-30.0% by weight, BACILLUS BACTERIA (Microbial Discovery Group) at 1.0-20.0% by weight. Once mixed, add to co-polymer blend, mix again and fill desired mold or container. This embodiment could be molded into almost any desired shape, including a boom or block shape. When made to float, this embodiment would aid in the process of removing organic debris from the holding pens used in aquaculture as well as improving water quality and clarity.

Active Ingredient Blend Example 7 (for Animal Waste Ponds):
  Mix PURIFIED WATER at 10.0-30.0% by weight, BACILLUS BACTERIA (Microbial Discovery Group) at 1.0-20.0% by weight, VIDET Q-3 SURFACTANT (Vitech International) at 0.1-5.0%, DYE (Keystone) in trace amounts. Once mixed, add to co-polymer blend, mix again, and fill desired mold or container. This embodiment could be molded into almost any desired shape, including a boom or block shape. When made to float, this embodiment would aid in the process of degrading liquefied animal waste collected in waste ponds on large farms and animal processing operations. This embodiment has the primary benefit of dispensing the ingredients at the water's surface over a period of time where they are most effective, particularly at reducing solids and controlling odor. This embodiment could also be made to sink in order to better degrade accumulated sludge and organic debris at the bottom of waste holding ponds or tanks Active Ingredient Blend Example 8 (for Treating Oil/Fuel Spills in Parking Lot Retention Ponds):
  Mix PURIFIED WATER at 10.0-30.0% by weight, BACILLUS BACTERIA (Microbial Discovery Group) at 1.0-20.0% by weight, VIDET Q-3 SURFACTANT (Vitech International) at 0.1-5.0%. Once mixed, add to co-polymer blend, mix again and fill desired mold or container. This embodiment could be molded into almost any desired shape, including a boom shape. When made to float, this embodiment aids in the process of degrading oil in oil spills on surface waterways, as well as parking lot run off in retention ponds. This embodiment has the primary benefit of dispensing the ingredients at the water's surface over a period of time where they are most effective at degrading floating oil and fuels that float on the surface of the catch basin ponds that collect rainwater run off of parking lots.

The following is an example of a complete formulation for a gel carrier that is effective in aquaculture applications and for treating ponds. Relative weight percentages are based on the total weight of the completed gel carrier (including both the co-polymer blend and the active ingredient blend). Representative suppliers of the components are identified but other components with similar characteristics and other suppliers could be used without departing from the invention. This example is not exclusive, there are many additional formulations that could be used as suitable gel carriers for aquaculture applications or for treating ponds without departing from the invention:

Co-polymer Blend:
  Polyamide gel SYLVACLEAR WF1500V (Arizona Chemical Company) at 25% by weight as the co-polymer and GLYCOL ETHER TPM (Dow Chemical) at 8% by weight as a polar solvent, heated to a minimum of 180° F. and mixed.

Active Ingredient Blend:
  Mix PURIFIED WATER at 22.75% by weight, VIDET Q-3 SURFACTANT (Vitech International) at 0.25% by weight, PROPYLENE GLYCOL (Dow Chemical) at 24% by weight, NITRIFYING BACTERIA (Aquafix) at 16% by weight, and BACILLUS BACTERIA (Microbial Discovery Group) at 4% by weight. The active ingredient blend is added to the co-polymer blend and mixed. The resulting mixture can be poured into a molded of almost any desired shape, e.g., the alligator head 32 shown in FIG. 6 or block shown in FIG. 4, and allowed to cool into a solid gel.

The foregoing examples are just a small sampling of the embodiments and applications of a gel carrier for releasing active ingredients. Embodiments of a gel carrier for releasing active ingredients could be used in numerous applications, including, but not limited to, use in connection with urinals, toilets, lift station or grease trap treatments, pond clarification, oil booms, and animal waste reduction.

Although the invention has been herein described in what is perceived to be the most practical and preferred embodiments, it is to be understood that the invention is not intended to be limited to the specific embodiments set forth above. Rather, it is recognized that modifications may be made by one of skill in the art of the invention without departing from the spirit or intent of the invention and, therefore, the invention is to be taken as including all reasonable equivalents to the subject matter of the appended claims and the description of the invention herein.

What is claimed is:

1. A gel carrier for releasing active ingredients into an aquaculture or pond environment comprising:
 a co-polymer blend formed by heating and mixing a polyamide gel and a polar solvent; and
 an active ingredient blend mixed with the co-polymer blend and formed into the gel carrier, the active ingredient blend comprising a mixture of water, surfactant, polar solvent, nitrifying bacteria, and bacillus bacteria;
 wherein the gel carrier is effectively insoluable in water-based liquids and at least the nitrifying bacteria and bacillus bacteria are released out of the gel carrier when the gel carrier is introduced to water-based liquids.

* * * * *